United States Patent [19]

Vescovo, Jr.

[11] Patent Number: 4,972,825
[45] Date of Patent: Nov. 27, 1990

[54] DISPOSABLE LARYNGOSCOPE COVER

[76] Inventor: Louis J. Vescovo, Jr., 2016 Pennington Gap, Memphis, Tenn. 38134

[21] Appl. No.: 249,506

[22] Filed: Sep. 26, 1988

[51] Int. Cl.⁵ .............................................. A61B 1/06
[52] U.S. Cl. ......................................... 128/10; 128/3; 383/103
[58] Field of Search ....................... 128/3, 4, 6, 10, 16, 128/7, 9, 15, 11, 17; 53/292, 585; 383/103, 63; D24/2

[56] References Cited

U.S. PATENT DOCUMENTS

| D. 242,396 | 11/1976 | Bauman | D24/2 |
|---|---|---|---|
| 2,247,258 | 6/1941 | Shepard | 128/16 |
| 2,576,322 | 11/1951 | Waters | 383/103 |
| 2,797,684 | 7/1957 | Moore | 128/9 |
| 2,854,004 | 9/1958 | Durrant | 128/11 |
| 2,913,030 | 11/1959 | Fisher | 383/63 |
| 3,112,031 | 11/1963 | Stewart . | |
| 3,146,775 | 9/1964 | Moore | 128/6 |
| 3,303,847 | 2/1967 | Eaton . | |
| 3,338,400 | 8/1967 | Edgworth . | |
| 3,349,764 | 10/1967 | Edinger | 128/16 |
| 3,426,749 | 2/1969 | Jephcott | 128/11 |
| 4,579,108 | 4/1986 | Bauman | 128/10 |
| 4,721,097 | 1/1988 | D'Amelio | 128/4 |
| 4,878,486 | 11/1989 | Slater | 128/11 |
| 4,884,558 | 12/1984 | Gorski | 128/11 |

FOREIGN PATENT DOCUMENTS 2169869 7/1986 United Kingdom ............... 383/103

Primary Examiner—Edward M. Coven
Assistant Examiner—Mark S. Graham
Attorney, Agent, or Firm—Walker & McKenzie

[57] ABSTRACT

A disposable cover for a laryngoscope. The cover includes a body having a hollow interior for receiving the laryngoscope, the body having a closed first end and an open second end; and closing structure for closing the second end of the body.

6 Claims, 2 Drawing Sheets

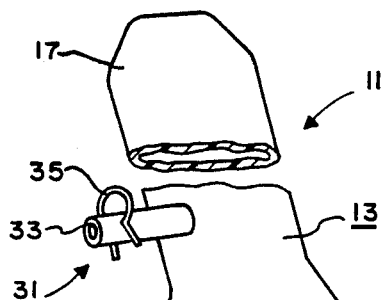
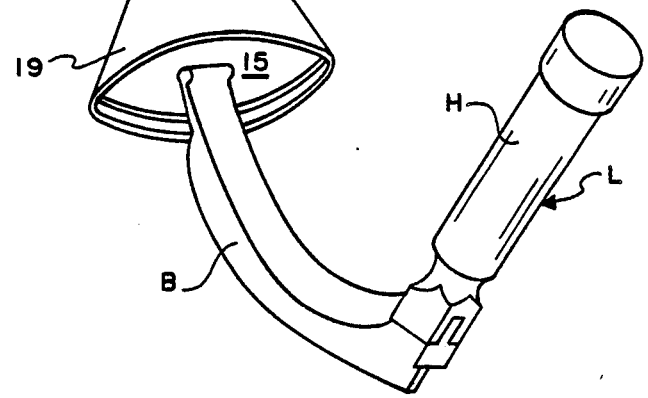
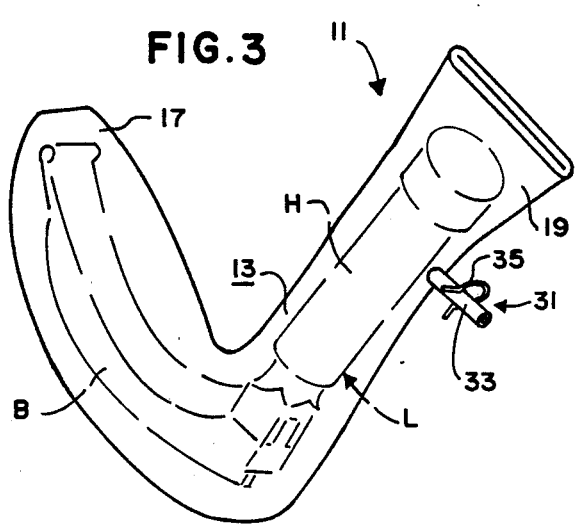
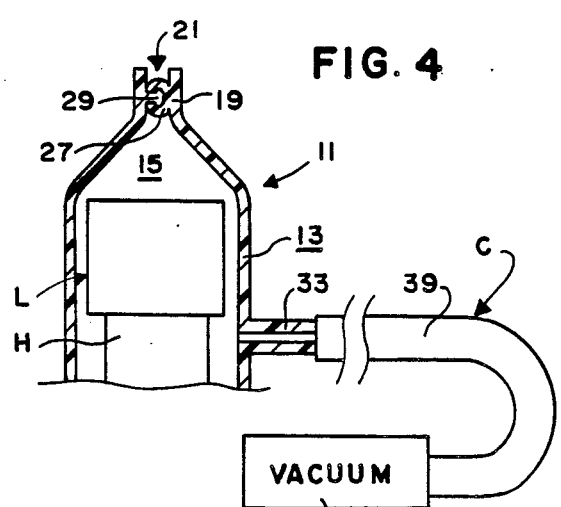
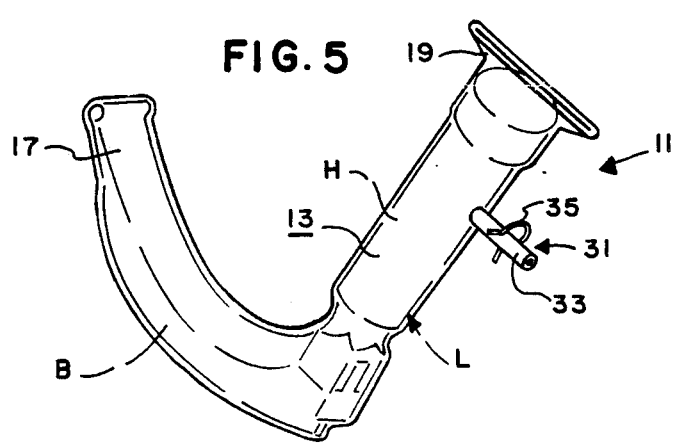

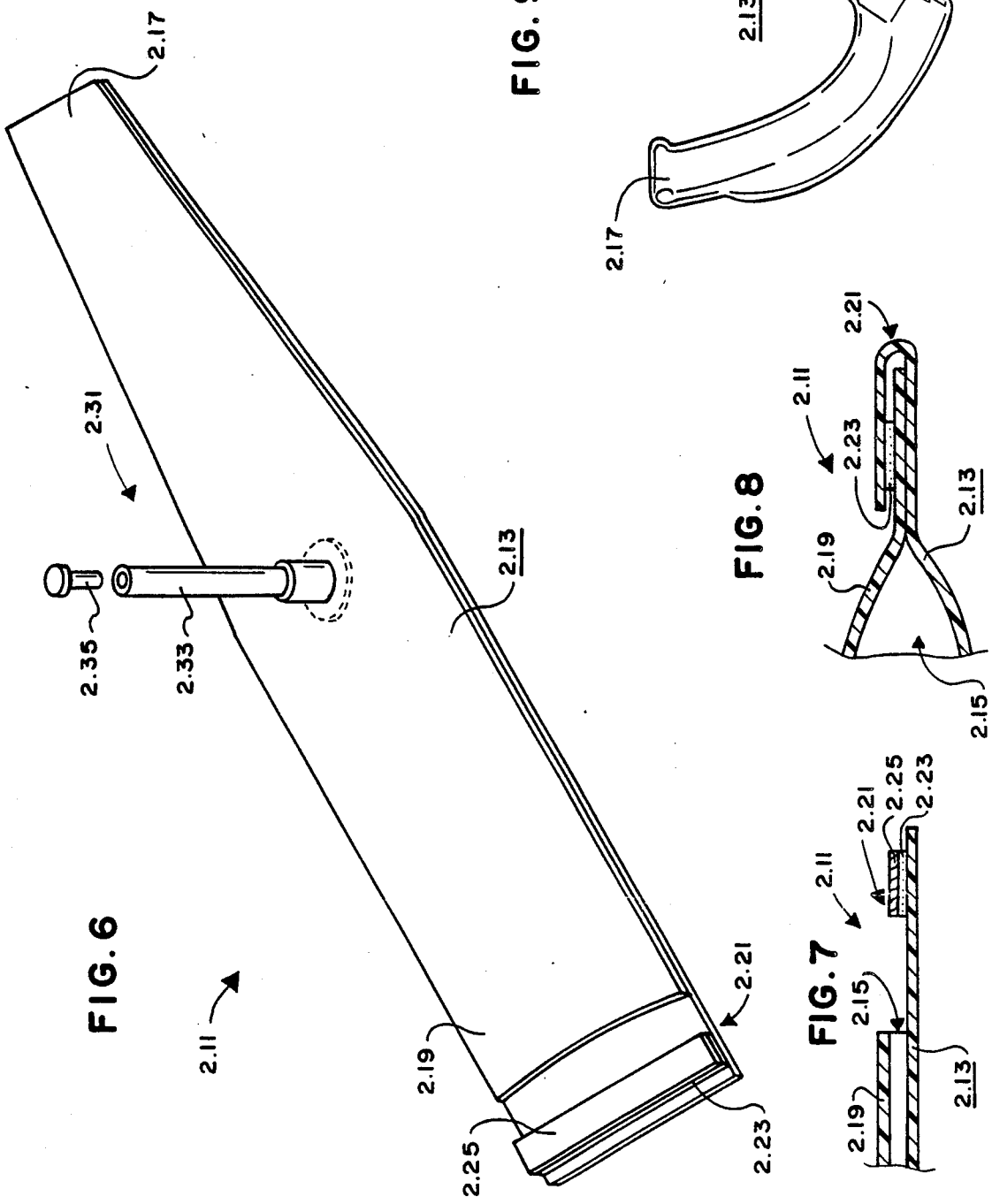

DISPOSABLE LARYNGOSCOPE COVER

BACKGROUND OF THE INVENTION

1. Field of the Invention: The present invention relates, in general, to disposable covers for medical instruments and more specifically to disposable covers for laryngoscopes.

2. Information Disclosure Statement: A preliminary patentability search in class 128, subclasses 10 and 11 disclosed the following patents: Shepard, U.S. Pat. No. 2,247,258, disclosing surgical instrument having a removable retractor end; Moore, U.S. Pat. No. 2,797,684, disclosing a disposable speculum cover; Durrant, U.S. Pat. No. 2,854,004, disclosing a laryngoscope blade; Steward, U.S. Pat. No. 3,112,031, disclosing a disposable package for catheters and the like; Moore et al, U.S. Pat. No. 3,146,775, disclosing a speculum having a disposable tip; Eaton, U.S. Pat. No. 3,303,847, disclosing a disposable container for dispensing cream and liquid materials; Edgworth et al, U.S. Pat. No. 3,338,400, disclosing a disposable package for surgical articles; Edinger et al, U.S. Pat. No. 3,349,764, disclosing a self-illuminating tongue depressor with a disposable tongue blade; Jephcott, U.S. Pat. No. 3,426,749, disclosing a disposable cover for a laryngoscope blade; Bauman, U.S. Pat. No. 4,579,108, disclosing a laryngoscope blade and disposable cover; and Bauman, U.S. Pat. Des. No. 242,396, disclosing an ornamental design for a disposable cover for a laryngoscope. None of the above patents disclose or suggest the present invention.

SUMMARY OF THE INVENTION

The present invention is directed toward providing an improved disposable cover for a laryngoscope. The disposable cover of the present invention includes a body having a hollow interior for receiving a laryngoscope, the body having a closed first end and an open second end; and closing means for closing the second end of the body.

BRIEF DESCRIPTION OF THE DRAWINGS

FIG. 1 is a perspective view of a first embodiment of the cover of the present invention showing a laryngoscope being inserted thereinto.

FIG. 2 is an enlarged sectional view of a portion of the cover of FIG. 1 showing the closing means thereof.

FIG. 3 is a perspective view of the cover of FIG. 1 showing a laryngoscope completely inserted thereinto.

FIG. 4 is an enlarged sectional view of a portion of FIG. 3 with a suction catheter coupled thereto.

FIG. 5 is a perspective view of the cover of FIG. 1 showing a laryngoscope completely inserted thereinto and with the air removed from the interior of the body of the cover.

FIG. 6 is a perspective view of a second embodiment of the cover of the present invention.

FIG. 7 is an enlarged sectional view of a portion of the cover of FIG. 6 showing the closing means thereof.

FIG. 8 is a sectional view similar to FIG. 7 but showing the closing means in a closed position.

FIG. 9 is a perspective view of the cover of FIG. 6 showing a laryngoscope completely inserted thereinto and with the air removed from the interior of the body of the cover.

DESCRIPTION OF THE PREFERRED EMBODIMENTS

A laryngoscope L typically includes a blade B and a handle H attached to the blade B. The present invention provides a disposable cover for the entire laryngoscope L, including the blade B and handle H.

A first embodiment of the cover of the present invention is shown in FIGS. 1-15 of the drawings and identified by the numeral 11. The cover 11 includes a body 13 having a hollow interior 15 for receiving the laryngoscope L. The body 13 has a closed first end 17 and an open second end 19. The body 13 is preferably constructed of a substantially clear and flexible material such as plastic in a tube-like shape. It should be noted that a typical laryngoscope L includes a light emitting means to aid the use thereof and the body 13 should be constructed of a sufficiently clear material which will not substantially hinder or affect light transmission therethrough. The second end 19 of the body 13 is preferably flared to allow the laryngoscope L to be easily inserted into the interior 15 thereof as clearly shown in FIG. 1.

The cover 11 includes closing means 21 for selectively closing the second end 19 of the body 13. The closing means 23 preferably forms an air-tight closure of the second end 19 of the body 13. The closing means 21 preferably includes a first closure member 23 attached to a portion of the second end 19 of the body 13 and preferably includes a second closure member 25 attached to a portion of the second end 19 of the body 13. The first and second closure members 23, 25 preferably coact with one another to form an air-tight seal for the second end 19 of the body 13. The first closure member 23 preferably includes a female portion 27 and the second closure member 25 preferably includes a male portion 29 for being snapped into the female portion 27 of the first closure member 23.

The cover 11 preferably includes a valve means 31 for allowing air to be removed from the interior 15 of the body 13 after the second end 19 of the body 13 has been closed to cause the body 13 to collapse about the laryngoscope L when air is removed from the interior 15 of the body 13 after the laryngoscope L has been inserted into the interior 15 of the body 13 and the second end 19 of the body 13 has been closed. The specific construction and operation of the valve means 31 may vary as will now be apparent to those skilled in the art. Preferably, the valve means 31 includes a tubular member 33 communicating with the interior 15 of the body 13 and preferably includes a clip member 35 for closing the tubular member 33. The tubular member 33 is preferably adapted to be coupled to a typical suction catheter C for allowing air to be removed from the interior 15 of the body 13 by the suction catheter C. The suction catheter C commonly includes a vacuum source 37 and a flexible tube 39 extending from the vacuum source 37 for being coupled to the distal end of the tubular member 33 as clearly shown in FIG. 4 to allow air to be drawn from the interior 15 of the body 13 in a manner as will now be apparent to those skilled in the art.

The specific construction and operation of the cover 11 may vary. Preferably, the body 13, closing means 21 and tubular member 33 are constructed as an integral, one-piece unit out of a substantially clear, flexible plastic with the body 13 and closing means 21 being similar in construction to a common "zip-lock" plastic bag. To use the preferred embodiment of the cover 11, the laryngoscope L is inserted into the interior 15 of the body 13 through the opened second end 19. The second end 19 is then closed by pressing the male portion 29 into the female portion 27 to form an air tight seal. The distal end of the tube 39 is then coupled to the distal end of the tubular member 33 with the clip member 35 removed therefrom and the vacuum source 37 activated to withdraw air from the interior 15 of the body 13 and cause the body 13 to collapse about the laryngoscope L. The clip member 35 is then attached to the tubular member 33 to close the tubular member 33 and form an air tight seal. The tube 39 can then be removed from the tubular member 33 and the laryngoscope L used in the typical manner. After use, the laryngoscope L can be removed from the cover 11 by merely opening the second end 19 of the body 13 and withdrawing the laryngoscope L. The cover 11 can then be discarded.

A second embodiment of the cover of the present invention is shown in FIGS. 6–9 of the drawings and identified by the numeral 2.11. The cover 2.11 is substantially similar to the cover 11 and includes a body 2.13 having a hollow interior 2.15 for receiving the laryngoscope L. The body 2.13 has a closed first end 2.17 and an open second end 2.19. The body 13 is preferably constructed of a substantially clear flexible plastic in a tube-like shape. At least the interior walls of the body 13 are preferably constructed so as to have a low coefficient of friction to allow the laryngoscope L to be easily inserted thereinto. More specifically, the body 2.13 is preferably constructed of any well known plastic which inherently has a low coefficient of friction and which does not substantially hinder or affect light transmission therethrough.

The cover 2.11 includes closing means 2.21 for selectively closing the second end 2.19 of the body 2.13. The closing means 2.23 preferably forms a substantially airtight closure of the second end 2.19 of the body 2.13. The closing means 2.21 preferably includes a length of double side tape 2.23 attached to a tab-like portion of the second end 2.19 of the body 13 and preferably includes a removable cover member 2.25 removably attached to the tape 2.23 to prevent inadvertent sticking of the tape 2.23. To close the second end 2.19 of the body 2.13, the cover member 2.25 is merely removed from the tape 2.23 and the tab-like portion folded back over the open mouth of the second end 2.19 of the body 2.13 until the tape 2.23 is secured as clearly shown in FIG. 8.

The cover 2.11 preferably includes a valve means 2.31 for allowing air to be removed from the interior 2.15 of the body 2.13 after the second end 2.19 of the body 2.13 has been closed to cause the body 2.13 to collapse about the laryngoscope L when air is removed from the interior 2.15 of the body 2.13 after the laryngoscope L has been inserted into the interior 2.15 of the body 2.13 and the second end 2.19 of the body 2.13 has been closed. The specific construction and operation of the valve means 2.31 may vary as will now be apparent to those skilled in the art. Preferably, the valve means 2.31 includes a tubular member 2.33 communicating with the interior 15 of the body 13 and preferably includes a plug member 2.35 for selectively closing the tubular member 2.33. The tubular member 2.33 is preferably adapted to be coupled to the suction catheter C for allowing air to be removed from the interior 2.15 of the body 2.13 by the suction catheter C in a manner as will now be apparent to those skilled in the art.

The specific construction and operation of the cover 2.11 may vary. Preferably, the body 2.13 and tubular member 2.33 are constructed as an integral, one-piece unit out of a substantially clear, flexible plastic with the tape 2.33 of the closing means 21 consisting of typical double sided tape will known to those skilled in the art. To use the preferred embodiment of the cover 2.11, the laryngoscope L is inserted into the interior 2.15 of the body 2.13 through the opened second end 2.19. The second end 2.19 is then closed by removing the cover member 2.25, folding back the tab-like portion and pressing the tape 2.23 against a portion of the body 13 to form a substantially air tight seal. The distal end of the tube 39 is then coupled to the distal end of the tubular member 2.33 with the plug member 2.35 removed therefrom and the vacuum source 37 activated to withdraw air from the interior 2.15 of the body 2.13 and cause the body 2.13 to collapse about the laryngoscope L. The tubular member 2.33 is then pinched closed, the tube 39 removed from the tubular member 2.33, and the plug member 2.35 pushed into the distal end of the tubular member 2.33 to closed the tubular member 2.33 and form an air tight seal. The laryngoscope L can then be used in the typical manner. After use, the laryngoscope L can be removed from the cover 2.11 by merely opening the second end 2.19 of the body 2.13 and withdrawing the laryngoscope L. The cover 2.11 can then be discarded.

Although the present invention has been described and illustrated with respect to preferred embodiments and a preferred use therefor, it is not to be so limited since modifications and changes can be made therein which are within the full intended scope of the invention.

I claim:

1. In combination with a suction catheter and a laryngoscope, a disposable cover for said laryngoscope, said cover comprising:
   a) a body having a hollow interior sized to receive all of said laryngoscope, said body having a closed first end and an open second end, said body being constructed of a clear and flexible plastic, said second end of said body being flared to allow said laryngoscope to be easily inserted into said interior of said body;
   b) closing means for closing said second end of said body and for forming an air-tight closure of said second end of said body, said closing means including a first closure member attached to a portion of said second end of said body and including a second closure member attached to a portion of said second end of said body, said first and second closure members coacting with one another to form an air-tight seal, said first closure member including a female portion, said second closure member including a male portion for being snapped into said female portion of said first closure member; and
   c) valve means for allowing air to be removed from said interior of said body after said second end of said body has been closed to cause said body to collapse about said laryngoscope when air is removed from said interior of said body after said laryngoscope has been inserted into said interior of said body and said second end of said body has been closed; said valve means including a tubular member communicating with said interior of said body and including a clip member for closing said tubular member, said tubular member being adapted to be coupled to said suction catheter for allowing air to be removed from said interior of said body by said suction catheter.

2. In combination with a suction catheter and a laryngoscope, a disposable cover for said laryngoscope, said comprising:
   a) a body having a hollow interior sized to receive all of said laryngoscope, said body having a closed first end and an open second end, said body being constructed of a substantially clear and flexible plastic, the interior walls of said body being substantially smooth for allowing said laryngoscope to be easily inserted into said interior of said body without substantial resistance;
   b) closing means for closing said second end of said body and for forming a substantially air-tight closure of of said second end of said body, said closing means including a length of tape attached to a portion of said second end of said body; and
   c) valve means for allowing air to be removed from said interior of said body after said second end of said body has been closed to cause said body to collapse about said laryngoscope when air is removed from said interior of said body after said laryngoscope has been inserted into said interior of said body and said second end of said body has been closed; said valve means including a tubular member communicating with said interior of said body and including a plug member for closing said tubular member, said tubular member being adapted to be couped to said suction catheter for allowing air to be removed from said interior of said body by said suction catheter.

3. In combination with a suction means and a laryngoscope, a disposable cover of said laryngoscope, said cover comprising:
   a) a body having a hollow interior sized to receive said laryngoscope, said body having a closed first end and an open second end, at least a portion of said body being constructed of a clear material; said hollow interior of said body, being sized to receive all of said laryngoscope;
   b) seal means for forming an air-tight seal at said second end of said body; and
   c) valve means for being coupled to said suction means and for allowing air to be removed from said interior of said body after said air-tight seal has been formed at said second end of said body to cause said body to collapse about said laryngoscope.

4. The combination of claim 3 in which all of said body is constructed of a clear and flexible plastic.

5. The combination of claim 4 in which the interior walls of said body are substantially smooth for allowing said larynoscope to be easily inserted into said interior of said body without substantial resistance.

6. In combination with a suction means and a laryngoscope, a disposable cover for said laryngoscope, said cover comprising:
   a) body having a hollow interior sized to receive said laryngoscope, said body having a closed first end and an open second end, at least a portion of said body being constructed of a clear material;
   b) seal means for forming an air-tight seal at said second end of said body; said seal means including a first closure member attached to a portion of said second end of said body and including a second closure member attached to a portion of said second end of said body, said first and second closure members coacting with one another to form an air-tight seal, said first closure member including a female portion, said second closure member including a male portion for being snapped into said female portion of said first closure member; and
   c) valve means for being coupled to said suction means and for allowing air to be removed from said interior of said body after said air-tight seal has been formed at said second end of said body to cause said body to collapse about said laryngoscope.

* * * * *